(12) United States Patent
Saied (10) Patent No.: US 7,213,596 B2
(45) Date of Patent: May 8, 2007

(54) PATIENT POSITIONING ASSISTANCE DEVICE

(76) Inventor: Victor Camal Saied, 2802 Hamilton Blvd., Wichita Falls, TX (US) 76038

( * ) Notice: Subject to any disclaimer, the term of this patent is extended or adjusted under 35 U.S.C. 154(b) by 484 days.

(21) Appl. No.: 10/338,594

(22) Filed: Jan. 8, 2003

(65) Prior Publication Data

US 2003/0098026 A1 May 29, 2003

Related U.S. Application Data

(63) Continuation-in-part of application No. 09/975,178, filed on Oct. 11, 2001, now Pat. No. 6,935,340.

(51) Int. Cl.
*A61G 15/00* (2006.01)

(52) U.S. Cl. ..................... 128/845; 128/846
(58) Field of Classification Search ............. 128/845, 128/846, 869–870; 602/18–19; 5/630, 646–650
See application file for complete search history.

(56) References Cited

U.S. PATENT DOCUMENTS

| | | | | |
|---|---|---|---|---|
| 3,732,863 A | * | 5/1973 | Harrington | 602/19 |
| 4,005,498 A | * | 2/1977 | Starr et al. | 5/81.1 R |
| D301,669 S | | 6/1989 | Dwelly | |
| 4,893,367 A | * | 1/1990 | Heimreid et al. | 5/632 |
| 5,184,365 A | * | 2/1993 | Stafford | 5/632 |
| 5,540,231 A | * | 7/1996 | Moy | 600/490 |
| 6,038,722 A | * | 3/2000 | Giori et al. | 5/709 |
| 6,065,166 A | | 5/2000 | Sharrock et al. | |
| 6,095,972 A | | 8/2000 | Sakamoto | |
| 6,123,666 A | | 9/2000 | Wrenn et al. | |
| 6,142,144 A | | 11/2000 | Pacey | |
| 6,174,281 B1 | | 1/2001 | Abramowitz | |
| 6,231,505 B1 | | 5/2001 | Martin | |
| 6,327,724 B1 | | 12/2001 | Sharrock et al. | |

OTHER PUBLICATIONS

World Wide Web, http://www.pocketpillow.net/, Pocket-Pillow, Courtesy Service Products, LTD, printed on Sep. 24, 2002, 4 pages.
World Wide Web, http://www.medslant.com/MED-about-1.htm, MEDSLANT, printed on Sep. 23, 2002, 2 pages.
World Wide Web, http://www.hygeco.com/english/00231.htm, Hygeco Inflatable Pillow, Hygeco 2000, printed on Sep. 24, 2002, 1 page.

(Continued)

*Primary Examiner*—Michael A. Brown
(74) *Attorney, Agent, or Firm*—Haynes and Boone, LLP (57) ABSTRACT

A patient positioning assistance device is disclosed. The patient positioning assistance device is placed under the head of a patient in a supine position during endotracheal intubation of the patient. The device comprises a base and an inflatable chamber slidably coupled to the base to facilitate positioning of the chamber under the head of the patient and being operable to adjust a tilt position of the head of the patient to facilitate insertion and proper placement of a laryngoscope blade into the mouth of the patient.

24 Claims, 4 Drawing Sheets

OTHER PUBLICATIONS

World Wide Web, http://www.hygeco.com/resource/products/highres/00231.jpg, printed on Sep. 24, 2002, 1 page.

World Wide Web, http://www.comfortchannel.com/prod.itml/icOid/568?source=googleeadwords, Sleepmatters Adjustable Air Pillow, printed on Sep. 24, 2002, 2 pages.

World Wide Web, http://www.safetycentral.com/inpilseatcus.html, Inflatable Pillow/Seat Cushion, 2002, printed on Sep. 24, 2002, 2 pages.

Elizabeth Douglas, "Some Hairstyles Can Complicate Intubation," Anesthesiology News, vol. 27, No. 8, Aug. 2001, pp. 1, 34.

* cited by examiner

PATIENT POSITIONING ASSISTANCE DEVICE

CROSS-REFERENCE TO RELATED APPLICATIONS

The present application is a continuation-in-part of U.S. application Ser. No. 09/975,178, entitled "Endotracheal Intubation Assistance Device", filed on Oct. 11, 2001 now U.S. Pat. No. 6,935,340, the disclosure of which is incorporated herein by reference.

TECHNICAL FIELD OF THE INVENTION

The present invention relates generally to the field of medical devices, and more particularly to a patient positioning assistance device.

BACKGROUND OF THE INVENTION

During and prior to surgery, a patient is often manipulated manually to properly position various parts of his or her body to facilitate the performance of certain medical procedures. For example, a patient's head and neck may be manipulated to facilitate the insertion of an endotracheal tube for intubation, a patient's head and shoulders may be manipulated and positioned for a thyroid operation, and a patient's torso may be manipulated to better present a breast for examination and surgery. The proper manipulation and/or placement of the patient's body is often necessary to prevent brachial plexus injury as in kidney or hip surgery.

Endotracheal intubation requires the insertion of a flexible tube through the oral cavity (or sometimes nasal cavity), the oropharynx, the glottis and into the trachea. Safe and successful intubation requires controlled insertion of the endotraeheal tube so that the tube is introduced through the glottis of the larynx without damaging the teeth or surrounding tissues such as oropharynx, epiglottis, vocal cords or laryngeal cartilages. It is desirable that the practitioner inserting the tube has a clear view of the glottis and vocal cords to guide the tube into the trachea successfully and without injury to the patient. It is sometimes difficult or even not possible to obtain a clear view of the glottis, so it is desirable that optimal positioning of the laryngoscope blade and the patient's head be attained for increasing the success of endotracheal intubation. The intubation process typically requires extending the head of the patient to facilitate insertion of the laryngoscope blade into the mouth. With the laryngoscope blade in place against the tongue of the patient, the practitioner uses the laryngoscope to lift the tongue and frequently lift the patient's head with the blade to expose the glottis into view.

There are several problems with the conventional manner in which endotracheal intubation is performed. Because the blade is used to lift and position the patient's head, there is a certain likelihood of trauma to the soft tissues of the patient's mouth, pharynx, vocal cords, laryngeal cartilages and to the teeth, leading to bleeding, sore throat, hoarseness or dislodgment or breakage of teeth. Furthermore, because the practitioner typically uses his/her weaker non-dominant hand to hold the laryngoscope handle and insert the laryngoscope blade so that the dominant hand can be used to insert the endotracheal tube, the practitioner often has difficulty lifting, supporting and manipulating the patient's head with the weaker non-dominant arm and hand. Therefore, in a substantial percentage of cases, the practitioner is required to request and wait for another person's, typically a nurse's, assistance in lifting the patient's head into optimal position. This person also frequently is asked to apply pressure on the front part of the neck over the cricoid cartilage for better visualization of the glottis and to prevent aspiration of gastric contents which can cause pneumonia, lung abscesses or even death. The necessity of calling for and requiring an assistant causes delay and interferes with the nurse's performance of his/her tasks in getting the surgical procedure underway.

In many other procedures, such as surgery in which the patient is required to assume and maintain a lateral position, such as kidney or hip surgery, the patient's axillary neurovascular structures may become damaged irreparably if the patient's body weight is improperly supported. During other surgical procedures such as thyroid gland surgery and anterior cervical spine surgery, the patient, lying in a supine position, must be positioned to provide better access to the anterior neck region. It is a common practice for medical personnel to simply roll up a towel or some other soft padding and place it under the patient. However, these rolls are often not optimal in size for safe positioning of the patient. Further, these towel rolls and padding cannot be easily adjusted to vary the height or orientation to modify the patient's position intraoperatively. Many other procedures may require the patient to assume a prescribed position in order to minimize risks or improve the performance of the procedures.

SUMMARY OF THE INVENTION

Accordingly, there is a desire for a device to assist during a surgical procedure, for example a device that aids in the proper placement and support of the patient's body to better present a surgical site during the surgical procedure.

In accordance with an embodiment of the present invention, a patient positioning assistance device is disclosed. The patient positioning assistance device is placed under the head of a patient in a supine position during endotracheal intubation of the patient. The device comprises a base and an inflatable chamber slidably coupled to the base to facilitate positioning of the chamber under the head of the patient and being operable to adjust a tilt position of the head of the patient to facilitate insertion and proper placement of a laryngoscope blade into the mouth of the patient.

In accordance with another embodiment of the present invention, a method to facilitate endotracheal intubation of a patient with a patient positioning assistance device placed under the head of the patient in a supine position is disclosed. The method comprises supporting the head of the patient on a chamber coupled to a base of the patient positioning assistance device, the chamber being inflatable to adjust the height of the head of the patient relative to the body of the patient, and sliding the chamber along the base in a predetermined direction and inflating the chamber to adjust a tilt position of the head of the patient to facilitate insertion and proper placement of a laryngoscope blade into the mouth of the patient.

In accordance with another embodiment of the present invention, a patient positioning assistance device is disclosed. The patient positioning assistance device is placed under the head and shoulders of the patient in a supine position. The device comprises a first chamber being inflatable to adjust the height of the head of the patient relative to the body of the patient; a second chamber being inflatable to adjust the height of a right side of the thorax of the patient, the second chamber being substantially orthogonal to the first chamber; and a third chamber being inflatable to adjust the height of a left side of the thorax of the patient, the third chamber being substantially orthogonal to the first chamber and substantially parallel and proximate to the second chamber.

In accordance with yet another embodiment of the present invention, a method to facilitate proper positioning of a patient during a surgical procedure with a patient positioning assistance device placed under the upper body of the patient in a supine position is disclosed. The method comprises supporting the head of the patient on a first chamber of the patient positioning assistance device, the first chamber being inflatable to adjust the height of the head of the patient relative to the body of the patient and independently inflating a second chamber and a third chamber of the patient positioning assistance device to adjust the relative height of the patient's right and left sides to provide access to a predetermined body portion of the patient to a surgeon performing the surgical procedure.

Other aspects of the invention will become apparent to those skilled in the art upon review of the following description of specific embodiments of the invention in conjunction with the accompanying figures.

BRIEF DESCRIPTION OF THE DRAWINGS

For a more complete understanding of the present invention, the objects and advantages thereof, reference is now made to the following descriptions taken in connection with the accompanying drawings in which.

DETAILED DESCRIPTION OF THE DRAWINGS

The preferred embodiment of the present invention and its advantages are best understood by referring to FIGS. 1 through 4 of the drawings.

Figure 1:
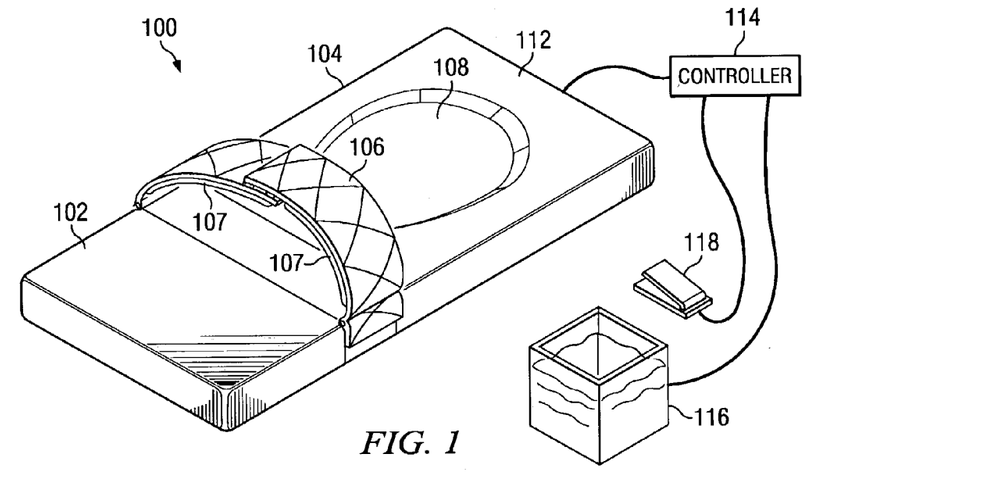
FIG. 1 is an isometric view of an endotracheal intubation assistance device according to a preferred embodiment of the present invention.

FIG. 1 is an isometric view of an endotracheal intubation assistance device 100 according to a preferred embodiment of the present invention. Intubation assistance device 100 is preferably a pillow, cushion, or support that has at least two independently adjustable chambers—a first chamber 102 and a second chamber 104. First chamber 102 and second chamber 104 are preferably coupled to each other to form an integral unit.

First chamber 102 of endotracheal intubation assistance device 100 is used to support the shoulder regions of a person, for example a patient to be intubated, and second chamber 104 is used to support the head of the patient. Second chamber 104 preferably includes a concave depression 108 on at least its upper surface 112 for "cupping" and providing stability to the head of the patient. Each of the two chambers is preferably air tight with gas-impermeable walls so that it is capable of being independently inflated and deflated. Inflation and deflation of the individual chambers 102 and 104 facilitates raising and lowering of the patient's head and shoulders supported by the respective chambers. If desired, chambers 102 and 104 may be independently manipulated or operated so as to raise and lower the head and shoulders of the patient. Although intubation assistance device 100 as shown in FIG. 1 is rectangular in shape the invention is not so limited and in alternative embodiments, intubation assistance device 100 may be of any shape.

If desired, intubation assistance device 100 may also include a pressure applicator 106. Pressure applicator 106 comprises a strap with an adjustable length. Pressure applicator 106 may include an inflatable elongated chamber 107 disposed along an inner surface of the strap. Pressure applicator 106 may be coupled to intubation assistance device 100 preferably close to the boundary of the two chambers 102 and 104 and may be adjusted to extend across upper surface 112 of intubation assistance device 100 around the neck of a patient. Pressure applicator 106 is used to apply pressure to a specific spot of the patient's neck when the neck is in a particular position as discussed herein below. Chamber 107 may be inflated to apply additional pressure, if necessary.

The inflation/deflation of chambers 102, 104 and 107 of intubation assistance device 100 may be controlled by a controller 114. In the preferred embodiment, controller 114 does not require the practitioner to use his/her hands for operating intubation assistance device 100 as it is desirable that the practitioner use his/her non-dominant hand to insert the laryngoscope and use the dominant hand to insert the endotracheal tube, into the patient's mouth. Thus, controller 114 may receive input from an actuating device 118, such as a foot pedal. If desired, controller 114 may be voice activated to follow the practitioner's verbal commands to inflate and deflate chambers 102, 104 and 107. Alternatively, controller 114 may be hand operated with actuating device 118 in proximity to the patient's head. In another alternative embodiment, actuating device 118, which is preferably a foot pedal, may be coupled to a bellows (not shown). By applying pressure on the foot pedal, air from the bellows may be used to inflate chambers 102, 104 and 107. The different chambers 102, 104 and 107 may be deflated by removing pressure from the foot pedal.

The different chambers 102, 104 and 107 of intubation assistance device 100 may be adapted to couple to a supply of inflatant 116 and a pump (not shown) under the control of controller 114 to inflate the different chambers 102, 104 and 107. The inflatant may be air, oxygen, nitrogen or any other suitable gases or liquids. One or more of chambers 102, 104 and 107 may comprise a self-expanding foam having a gas-impermeable outer barrier and an inner foam cell structure which may be deflated by evacuating air from the cells therein. Deflation of the foam causes deflation of the chamber. Upon releasing the suction, the foam expands with incoming ambient air and returns to its original size. Inflatant supply 116 may comprise a tank located in the operating room itself or a central supply and may be associated with an anesthesia machine. Preferably, each of the chambers 102, 104 and 107 is individually coupled to inflatant supply 116 to allow each chamber to be independently inflated and deflated. Thus, for example the practitioner may inflate first chamber 102 to a desired degree to facilitate insertion of the laryngoscope blade into the mouth of the patient. The practitioner may deflate first chamber 102 and inflate second chamber 104 to a different degree to raise the head of the patient to facilitate viewing the glottis of the patient for insertion of an endotracheal tube. Chamber 107 may be inflated independently of or with inflation of second chamber 104. One or more outlet valves (not shown) may be provided to allow each chamber to be independently deflated.

Intubation assistance device 100 is preferably a portable device separate from an operating table. However, if desired, it may be incorporated in a headrest of the operating table, a stretcher, a gurney and other apparatus.

Figure 2A:
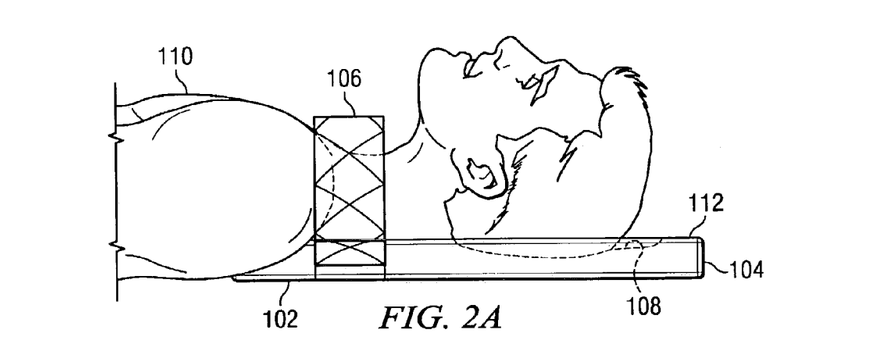
FIGS. 2A–2D illustrate the sequential operation of the endotracheal intubation assistance device of FIG. 1 according to a preferred embodiment of the present invention.

FIGS. 2A–2D illustrate the sequential operation of endotracheal intubation assistance device 100 according to a preferred embodiment of the present invention. In FIG. 2A, a patient 110 to be intubated is shown lying in a supine position with his head supported on upper surface 112 of intubation assistance device 100. The head of patient 110 rests in depression 108 of second chamber 104. Intubation assistance device 100 as shown in FIG. 2A is deflated or in its initial operating mode. If desired, intubation assistance device 100 may be used as a pillow for the head of patient 110 with second chamber 104 being partially inflated for the patient's comfort. If desired, first chamber 102 may be initially inflated to elevate the shoulders of patients who have tightly woven and firmly attached hairpieces to the occipital portion of the head. With the patient in the supine position, it is extremely difficult to insert the laryngoscope blade into the mouth unless the shoulders are elevated. Pressure applicator 106 is shown loosely fastened around the patient's neck, but need not be fastened at this point.

Figure 2B:
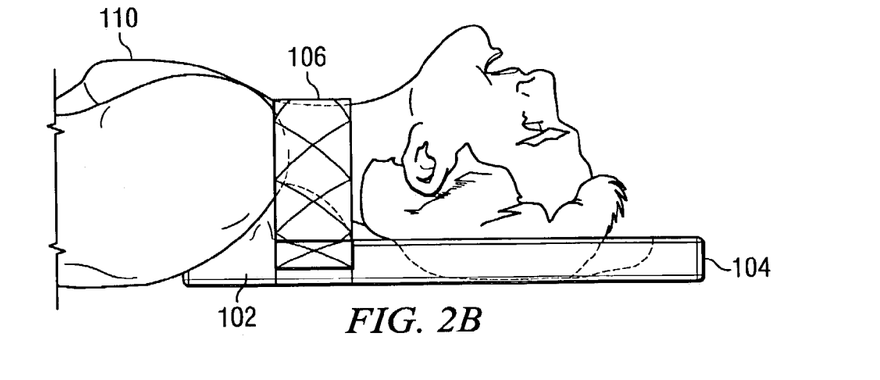

In FIG. 2B, the practitioner has raised first chamber 102 to elevate the shoulders of patient 110. First chamber 102 may be raised by inflating the chamber. In this position, the patient's head is extended and tilted back with the chin elevated tending to open the patient's mouth. Once the shoulders of the patient have been raised and the head extended, a laryngoscope blade may be more conveniently inserted into the mouth of the patient for the purpose of holding the patient's mouth open and displacing the patient's tongue. First chamber 102 may be inflated to a predetermined height or a height adjustable by the practitioner.

Figure 2C:
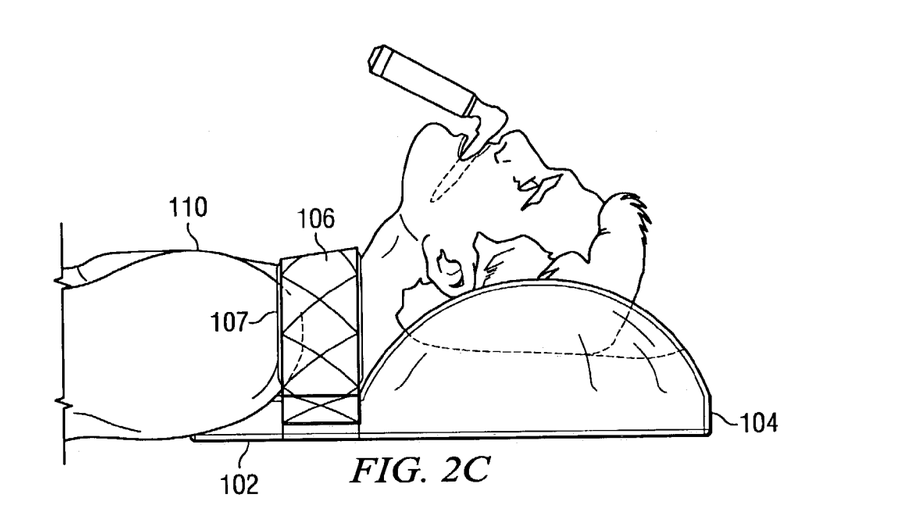

In FIG. 2C, second chamber 104 is in a raised position while first chamber 102 is in a lowered position. Second chamber 104 may be raised by inflating the chamber. First chamber 102 may be lowered by deflating the chamber. The inflation of second chamber 104 causes the head of the patient to be raised. Second chamber 104 may be inflated to a predetermined height or a height adjustable by the practitioner. By adjusting the amount of inflation of second chamber 104, the head of the patient is raised to a desired "sniffing" position to facilitate viewing the glottis of the patient for endotracheal intubation. At the same time, pressure applicator 106, fastened properly around the patient's neck, applies pressure to the cricoid cartilage of the neck. In this manner, pressure is applied to the cricoid and against the esophagus thereby preventing stomach contents of the patient from entering the pharynx and lungs. Applying pressure to the cricoid cartilage also facilitates visualization of the glottis and is particularly useful in patients with an anatomically anterior situated larynx. Chamber 107 may be inflated or deflated to adjust the pressure applied to the cricoid cartilage. Thus, aspiration of the gastric contents into the lungs of the patient is avoided. Inadvertent aspiration of gastric contents may cause pneumonia, lung abscesses or even death of the patient. Pressure applicator 106 may be properly fastened around the patient's neck at any point prior to insertion of the endotracheal tube into the patient's mouth, for example when intubation assistance device 100 is in its initial operating mode as shown in FIG. 2A. Thus, by utilizing intubation assistance device 100, the head of the patient may be oriented and raised to a desired position thereby making it easier and safer for the practitioner to intubate the trachea. Once the patient's head is in the desired position, the endotracheal tube may be inserted into the patient's mouth and placed in the proper position in the trachea.

Figure 2D:
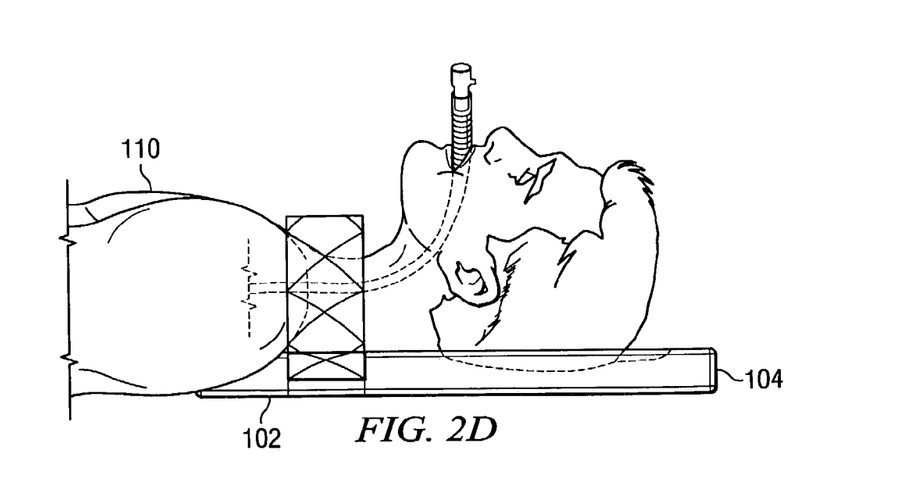

As shown in FIG. 2D, once the laryngoscope and the endotracheal tube are in the desired position, chamber 107 may be deflated and chambers 102 and 104 of intubation assistance device 100 may be lowered to put the patient's head in a normal position. Chambers 102 and 104 may be lowered by deflating chambers 102 and 104.

By using intubation assistance device 100, it is easier for the practitioner to intubate the patient as the practitioner does not have to use the force of the laryngoscope blade alone in order to lift and manipulate the head of the patient to the desired position. Therefore, the number of incidents of trauma and injury to the patient is significantly lowered. Furthermore, the delay associated with waiting for another person to provide assistance is avoided. Moreover, because the intubation assistance device of the present invention is intended to assist the practitioner in intubating a patient, the need for an assistant to perform this function is reduced or completely eliminated.

Although in the preferred embodiment, chambers 102 and 104 are raised and lowered by inflating and deflating the chambers, the invention is not so limited. In alternative embodiments, a mechanical system may be provided to raise and lower the chambers. For example, the two chambers may be supported on separate platforms (not shown). In such an embodiment, each of the platforms may be raised or lowered independently of the other platform. Thus, the two chambers 102 and 104 may be raised or lowered independently of each other.

The preferred embodiment endotracheal intubation assistance device aids in placement and support of the patient's head in an optimal position for endotracheal intubation without undue trauma to the patient's tissues and teeth that may otherwise result due to dependence on the laryngoscope blade alone to accomplish the desired head positioning. Furthermore, the need for another person's assistance is avoided. The preferred embodiment endotracheal intubation assistance device increases the probability of successful intubation without the use of specialized intubating equipment, such as special laryngoscopic equipment and/or intubating bronchoscopes.

Figure 3A:
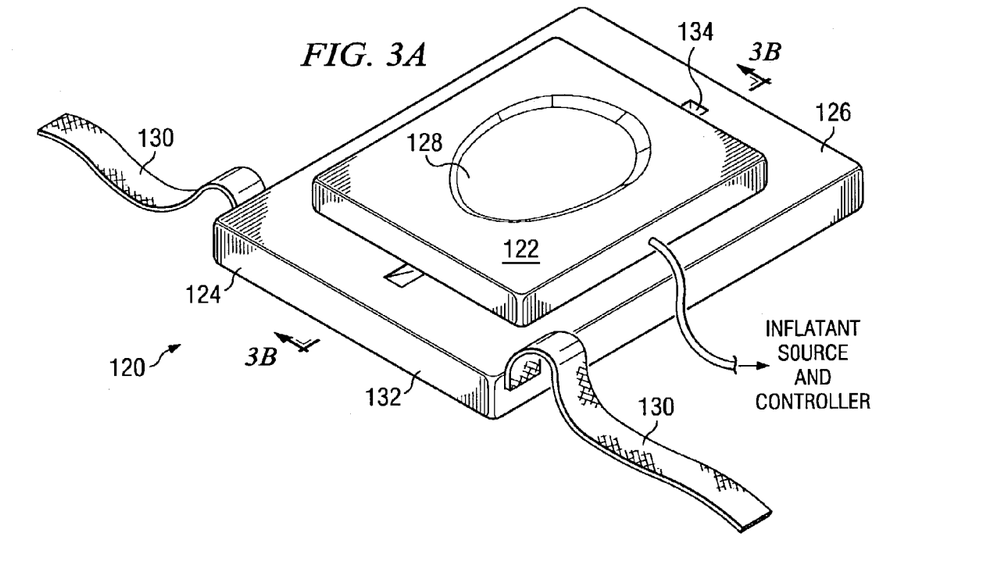
FIG. 3A is an isometric view of a patient positioning assistance device in accordance with an embodiment of the present invention.

FIG. 3A is an isometric view of a patient positioning assistance device 120 in accordance with an embodiment of the present invention. Patient positioning assistance device 120 may be used to properly position a portion of a patient's body during a surgical procedure, for example during endotracheal intubation. Patient positioning assistance device may also be referred to as an endotracheal intubation assistance device.

Figure 3B:
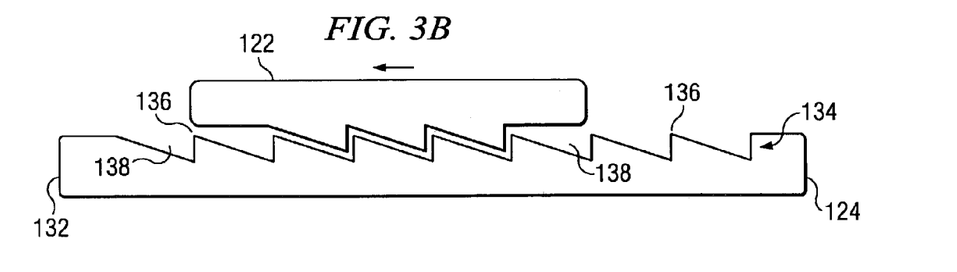
FIG. 3B is a sectional view of the patient positioning assistance device taken along section 1—1 of FIG. 3A with the chamber deflated.
Figure 3C:
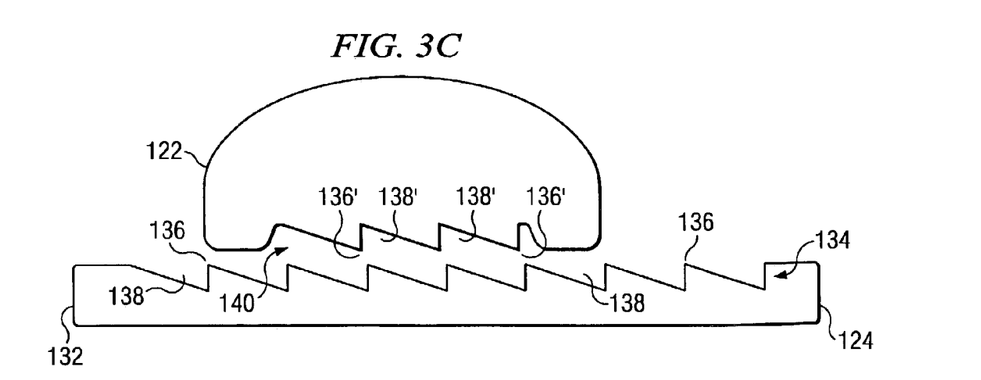
FIG. 3C is a sectional view of the patient positioning assistance device taken along section 1—1 of FIG. 3A with the chamber inflated.

Patient positioning assistance device 120 is preferably a pillow, cushion, or support that has at least one adjustable chamber, for example chamber 122. Device 120 preferably comprises a base 124. Chamber 122 may be part of base 124 or be disposed on a surface 126 of base 124. Chamber 122 is preferably used to support the head of a person. If desired, chamber 122 may include a concave depression 128 on at least its upper surface for "cupping" and providing stability to the head of the patient. In one embodiment of the present invention as shown in FIGS. 3A–3C, base 124 supports chamber 122 and extends just a short distance beyond the boundaries of the chamber. Alternatively, the inflatable chamber may be incorporated into a larger base, a stretcher, a surgical table, a bed, a gurney and other suitable surfaces.

If desired, device 120 may include a pressure applicator 130. Pressure applicator 130 comprises a strap with an adjustable length. Pressure applicator 130 may be coupled to base 124 preferably close to an end 132 of base 124. Pressure applicator 130 may be adjusted to extend across surface 126 of device 120 around the neck of a patient. Pressure applicator 130 is used to apply pressure to a specific spot of the patient's neck, for example the cricoid cartilage, when the neck is in a particular position. Pressure applicator 130 may include an inflatable elongated chamber (not shown) disposed along an inner or outer surface of the strap. The elongated chamber may be inflated to apply additional pressure, if desired.

If desired, one or more base tracks 134 may be provided on base 124. In the illustrated embodiment, chamber 122 is slidably coupled to base track 134. The slidable coupling of chamber 122 to base track 134 enables chamber 122 to travel along the base track. Thus, depending on the application, chamber 122 may be displaced towards or away from end 132 of base 124 to facilitate patient head positioning and orientation. For example, during an endotracheal intubation operation, chamber 122 may be inflated and moved towards end 132 to tilt the head of the patient back at a desired angle so that the head of the patient resting on chamber 122 is in an optimum safe extension position. In this position it is easier for the operator, for example an anesthesiologist, to insert the laryngoscope blade into the mouth of the patient.

It is desirable to make it easier for the operator to slide chamber 122 along base track 134 in a particular direction. For example, in the embodiment of FIGS. 3A–3C, it is desirable that it be easier to slide chamber 122 toward end 132 then away from end 132. The track mechanism is explained in further detail hereinbelow especially with reference to FIGS. 3B and 3C. Alternatively, chamber 122 may be maintained in its position or prevented from moving in a direction away from end 132 of base 124 by frictional forces that may be present between an underside of chamber 122 and surface 126 of base 124 in combination with the weight of the head and/or shoulders of the patient on chamber 122. FIG. 3B is a sectional view of patient positioning assistance device 120 taken along section 1—1 of FIG. 3A with chamber 122 deflated and FIG. 3C is a sectional view of patient positioning assistance device 120 taken along section 1—1 of FIG. 3A with chamber 122 inflated. In FIGS. 3B and 3C, base track 134 is shown recessed in base 124. If desired, base track 134 may be protruding from base 124.

Base track 134 is adapted to facilitate sliding motion of chamber 122 along the track. At least a portion of an underside of chamber 122 is adapted to facilitate sliding of chamber 122 along base track 134. Preferably, a chamber track 140 is provided on at least a portion of the underside of chamber 122. Base track 134 of base 124 preferably comprises a plurality of ridges 136 and a plurality of valleys 138 and chamber track 140 of chamber 122 comprises a plurality of ridges 136' and a plurality of valleys 138'. Preferably, ridges 136 and 136' are oriented in a manner that makes it easier for the operator to slide chamber 122 along base track 134 in a direction toward end 132 of base 124 as shown by the arrow in FIG. 3B.

During a procedure, such as endotracheal intubation, initially chamber 122 is in a deflated position with the patient in a supine position and the head of the patient supported by chamber 122. When chamber 122 is in the deflated position, as illustrated in FIG. 3B, chamber 122 may be moved along base track 134 such that ridges 136' of chamber track 140 interface with corresponding valleys 138 of base track 134 and ridges 136 of base track 134 interface with corresponding valleys 138' of chamber track 140. In the deflated position, not only can chamber 122 be moved along base track 134 in the direction of the arrow but also the interfacing of the tracks and valleys makes it difficult or prevents chamber 122 from sliding back in a direction away from end 132 of base 124.

The operator may slide chamber 122 under the head of the patient toward end 132 of base 124 to a desired extent. Once chamber 122 is in a desired position, the operator may adjust the height of chamber 122, for example by inflating chamber 122, to a desired height to facilitate tilting of the head of the patient to a desired degree to make it easier for the operator to insert the laryngoscope blade into the mouth of the patient. Among other things, inflation of chamber 122 causes the underside of chamber 122 surrounding chamber track 140 to expand. This expansion causes chamber track 140 to be raised in a manner that causes chamber track 140 to disengage from base track 134 of base 124. In this position, as shown in FIG. 3C, ridges 136 of base track 134 do not interface with valleys 138' of chamber track 140 and ridges 136' of chamber track 140 do not interface with valleys 138 on base track 134. Thus, if desired, the operator of device 120 may make minor changes in the position of chamber 122 by moving it toward or away from end 132 to further adjust the position and tilt of the head of the patient in a manner that makes it easier for the operator to insert the laryngoscope blade into the mouth of the patient.

Figure 4:
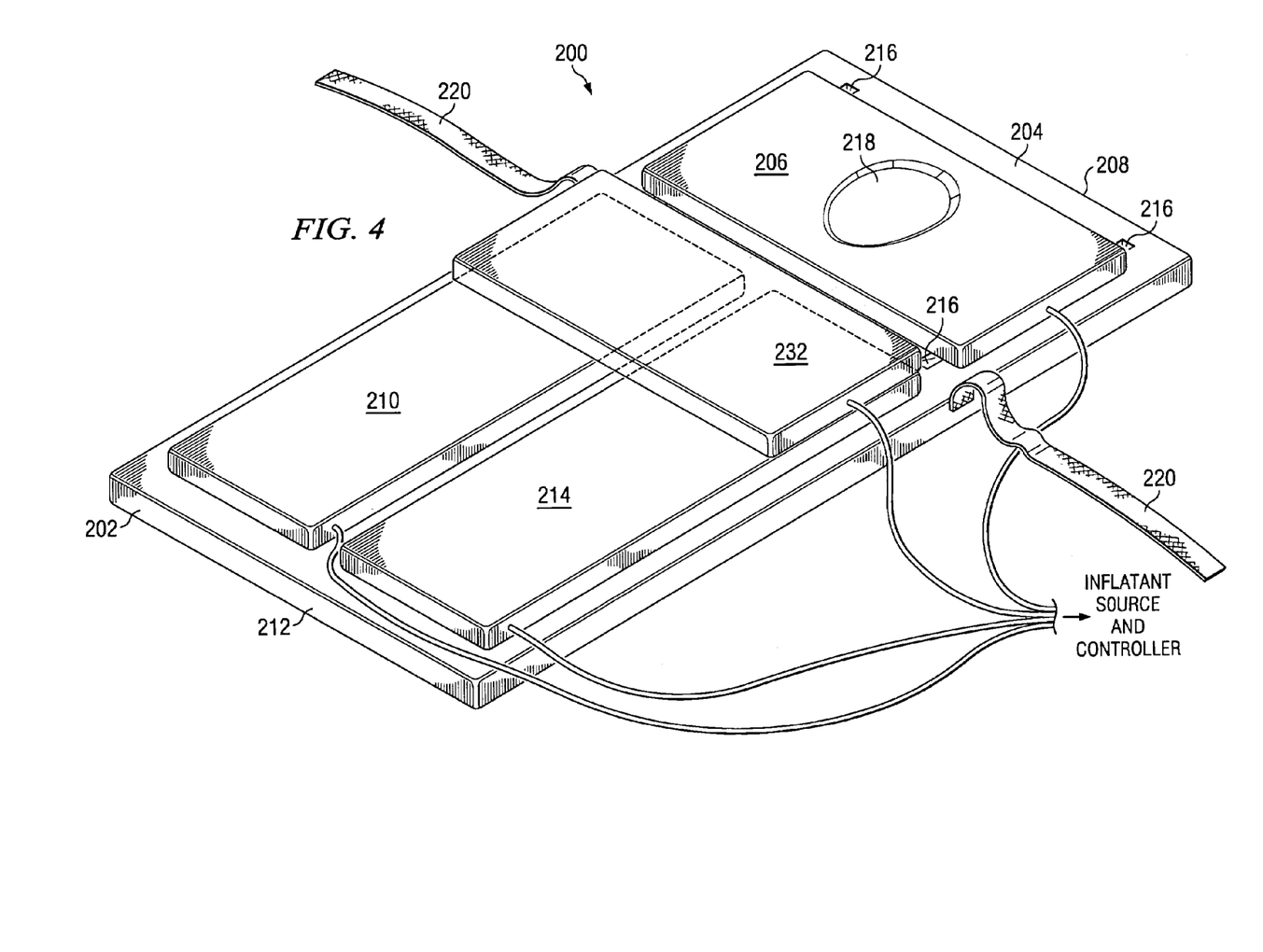
FIG. 4 is an isometric view of a patient positioning assistance device in accordance with an alternative embodiment of the present invention.

FIG. 4 is an isometric view of a patient positioning assistance device 200 in accordance with an alternative embodiment of the present invention. Patient positioning assistance device 200 is preferably a pillow, cushion, or support that has at least three independently adjustable chambers, for example a first chamber 206, a second chamber 210 and a third chamber 214. Device 200 preferably comprises a base 202. The chambers may be part of base 202 or be disposed on a surface 204 of base 202. First chamber 206 is preferably disposed along a first axis of base 202. In the illustrated embodiment, first chamber 206 is located near a first end 208 of device 200, but base 202 may extend substantially beyond first chamber 206. First chamber 206 is preferably used to support the head of a person, for example a patient. If desired, first chamber 206 may include a concave depression 218 on at least its upper surface for "cupping" and providing stability to the head of the patient.

Second chamber 210 may be disposed along a second axis of base 202, where the first and second axes are perpendicular with one another. Second chamber 210 extends a predetermined length along the second axis toward a second end 212 opposite first end 208. Preferably, the orientation of second chamber 210 is substantially orthogonal to first chamber 206. Second chamber 210 is preferably used to support a first side of the patient's upper body when the patient is in a supine position. Third chamber 214 may be disposed along the second axis of base 202 along side second chamber 210. Preferably, the orientation of third chamber 214 is substantially orthogonal to first chamber 206 and substantially parallel to second chamber 210. Third chamber 214 is preferably used to support a second side of the patient's upper body when the patient is in a supine position. In one embodiment of the invention as shown in FIG. 4, base 202 supports chambers 206, 210 and 214 and extends just a short distance beyond the boundaries of the chambers. Alternatively, the inflatable chambers of the present invention may be incorporated into a larger base, a stretcher, a surgical table, a bed, a gurney and other suitable surfaces.

If desired, a fourth chamber 232 may be disposed along the first axis of base 202 on top of second chamber 210 and third chamber 214. Preferably, the orientation of fourth chamber 232 is substantially parallel to first chamber 206 and substantially orthogonal to second chamber 210 and third chamber 214. If desired, fourth chamber 232 may be disposed below second chamber 210 and third chamber 214. Fourth chamber 232 is preferably used to support the shoulders of the patient when the patient is in a supine or lateral position. If desired, each of the chambers 206, 210, 214 and 232 may be replaced by a plurality of chambers to provide more control to the operator.

If desired, one or more tracks 216 may be provided on base 202. In the illustrated embodiment, first chamber 206 is slidably coupled to track 216. The slidable coupling of first chamber 206 to track(s) 216 enables first chamber 206 to travel along the track(s). Thus, depending on the application, first chamber 206 may be displaced toward or away from second and third chambers 210 and 214 to facilitate patient head/body positioning and orientation. For example, during an endotracheal intubation operation, first chamber 206 may be moved toward second and third chambers 210 and 214 and inflated so that the head of the patient resting on first chamber 206 is in an optimum safe extension position. In this position it is easier for the operator to insert the laryngoscope blade into the mouth of the patient. Although not illustrated, second chamber 210 and third chamber 214 may be coupled to tracks oriented along the second axis of base 202 so that second chamber 210 and/or third chamber 214 may be moved along the tracks to a desired position on base 202 to further facilitate patient support and orientation. Second chamber 210 and third chamber 214 may be coupled to the same or different tracks.

If desired, device 200 may also include a pressure applicator 220. Pressure applicator 220 comprises a strap with an adjustable length. Pressure applicator 220 may be coupled to device 200 preferably close to the boundary between first chamber 206 and second and third chambers 210 and 214. Pressure applicator 220 may be adjusted to extend across surface 204 of device 200 around the neck of a patient. Pressure applicator 220 is used to apply pressure to a specific spot of the patient's neck when the neck is in a particular position. Pressure applicator 220 may include an inflatable elongated chamber (not shown) disposed along an inner or outer surface of the strap. The elongated chamber may be inflated to apply additional pressure, if desired.

Each of the chambers is preferably air tight with gas-impermeable walls. Each chamber is capable of being independently inflated and deflated. The inflation/deflation of the chambers of device 120 and/or device 200 may be controlled in a manner similar to that described for controlling inflation/deflation of the chambers of the endotracheal intubation assistance device of FIG. 1, for example by coupling them to an inflatant source and a controller. Furthermore, if desired, the different chambers may be coupled to a source of inflatant already present in an operating room during surgery, for example an inflatant source that is associated with an anesthesia machine (not shown). The inflatant may be air, oxygen, nitrogen, and/or the like. An advantage of using an existing anesthesia machine for this purpose is that additional equipment is not needed to operate device 120 and/or device 200. This not only results in cost savings, but also reduces the number of equipments in the operating room.

Inflation and deflation of first chamber 206 of device 200 relative to the other chambers facilitates raising and lowering of the patient's head. Inflation and deflation of second chamber 210 relative to the other chambers facilitates raising and lowering of the right side of the patient's body. Inflation and deflation of third chamber 214 relative to the other chambers facilitates raising and lowering of the left side of the patient's body. Inflation and deflation of fourth chamber 232 relative to the other chambers facilitates raising the chest of a patient in the lateral position to prevent injury to the nerves in the axilla.

By inflating second chamber 210 to a desired height, a surgical site on the right side of the patient's body may be presented to the surgeon at a desired angle. For example, when surgery is performed on the right breast of the patient, the patient's body may be oriented by inflating second chamber 210 to a desired height to present the right breast at a desired angle to the surgical staff. By inflating third chamber 214 to a desired height, a surgical site on the left side of the patient's body may be presented to the surgeon at a desired angle. For example, when surgery is performed on the left breast of the patient, the patient's body may be oriented by inflating third chamber 214 to a desired height to present the left breast at a desired angle to the surgical staff.

During a surgical operation where it is desirable to have the patient on its side in a lateral position, for example during hip surgery or kidney surgery, the upper body of the patient has to be manually lifted to place a towel or axillary roll under the chest of the patient to prevent pressure on the nerves in the axilla. Inflating fourth chamber 232 of device 200 allows raising of the chest of the patient to a desired height to prevent injury to nerves in the axilla. Thus, device 200 may be used in place of the axillary roll used in existing procedures. The advantage of using device 200 in such an operation is that it is more precise, more comfortable and easier to use than the axillary roll. Furthermore, the height of the chambers may be easily adjusted intraoperatively.

During other surgical operations, such as thyroid gland surgery, anterior cervical spine operations, and/or the like, a towel or sheet roll is placed under the shoulder of the patient in a supine position to lift the shoulder and allow the head to be extended to give better access to the anterior neck. The roll size is different for each patient. If the roll is not of the right size, redoing of the roll to make it larger or smaller is required. Also, towards the end of the surgery the roll may have to be removed from under the shoulder for easier closing of the skin of the patient. Using device 200, fourth chamber 232 may be inflated to the desired height for optimal positioning of the patient to provide better access to the anterior neck of the patient to the surgeon. Alternatively or in addition, second chamber 210 and/or third chamber 214 may be inflated to adjust the shoulders of the patient to the desired height. Additionally, towards the end of the surgery to lower the shoulders of the patient, the inflated chambers may be simply deflated to a desired height to facilitate easier closing of the skin of the patient. For procedures, such as endotracheal intubation, device 200 may be used in a manner similar to intubation assistance device 100 of FIG. 1, by controlling the inflation/deflation of first chamber 206 and fourth chamber 232, thereby facilitating proper positioning of the patient for the procedure.

Although device 120 as shown in FIGS. 3A–3C and device 200 as shown in FIG. 4 are rectangular in shape, in alternative embodiments, device 120 and/or device 200 may be of any shape. Device 120 and/or device 200 are preferably portable devices separate from an operating table. However, if desired, the devices may be incorporated in a headrest of the operating table, a stretcher, a gurney or other apparatus.

Although in the illustrated embodiments, chambers 122, 206, 210, 214 and 232 are raised and lowered by inflating and deflating the chambers, in an alternative embodiment, a mechanical system may be provided to raise and lower the chambers. For example, each of the chambers may be supported on a separate platform (not shown). In such an embodiment, each of the platforms may be raised or lowered independently of the other platforms. Thus, chambers 122, 206, 210, 214 and 232 may be raised or lowered independently of each other.

While the invention has been particularly shown and described by the foregoing detailed description, it will be understood by those skilled in the art that various other changes in form and detail may be made without departing from the spirit and scope of the invention.

What is claimed is:

1. A method to facilitate endotracheal intubation of a patient with a patient positioning assistance device placed under the head of the patient in a supine position, comprising:
   supporting the head of the patient on a chamber coupled to a base of said patient positioning assistance device, said chamber being inflatable to adjust the height of the head of the patient relative to the body of the patient; and
   sliding said chamber along said base in a predetermined direction and inflating said chamber to adjust a tilt position of the head of the patient to facilitate insertion and proper placement of a laryngoscope blade into the mouth of the patient.

2. The method of claim 1, wherein said sliding step comprises sliding said chamber along a base track disposed on an upper surface of said base.

3. The method of claim 1, further comprising coupling said chamber to a supply of inflatant.

4. The method of claim 1, further comprising coupling said chamber to an inflatant source associated with an anesthesia machine.

5. The method of claim 4, wherein said inflatant is selected from the group consisting of air, oxygen, and nitrogen.

6. The method of claim 1, farther comprising coupling said chamber to a suction device operable to remove air from said chamber thereby causing said chamber to deflate.

7. The method of claim 1, further comprising activating an inflatant supply to provide an inflatant to said chamber to inflate said chamber.

8. The method of claim 1, further comprising disabling a suction device to allow a self-expending foam of said chamber to expand thereby causing inflation of said chamber.

9. The method of claim 1, further comprising controlling an amount of said inflatant supplied to said chamber to adjust the height of the patient's head relative to the body of the patient.

10. The method of claim 9, wherein controlling an amount of said inflatant comprises receiving an actuation signal from a foot pedal.

11. The method of claim 9, wherein controlling an amount of said inflatant comprises receiving an actuation signal from a hand operated unit.

12. The method of claim 9, wherein controlling an amount of said inflatant comprises receiving an actuation signal from a voice activated unit.

13. The method of claim 1, further comprising applying pressure on a foot pedal coupled to a bellows to supply air from said bellows to said chamber to inflate said chamber.

14. A method to facilitate proper positioning of a patient during a surgical procedure with a patient positioning assistance device placed under the upper body of the patient in a lateral position, comprising:
   supporting the head of the patient on a first chamber of said patient positioning assistance device, said first chamber being inflatable to adjust the height of the head of the patient relative to the body of the patient;
   independently inflating a second chamber and a third chamber of said patient positioning assistance device to adjust the relative height of the patient's right and left sides to provide access to a predetermined body portion of the patient to a surgeon performing said surgical procedure; and
   independently inflating a fourth chamber disposed on said second and third chambers to prevent injury to nerves in the axilla of the patient in the lateral position.

15. A method to facilitate proper positioning of a patient during a surgical procedure with a patient positioning assistance device placed under the upper body of the patient in a lateral position, comprising:
   supporting the head of the patient on a first chamber of said patient positioning assistance device, said first chamber being inflatable to adjust the height of the head of the patient relative to the body of the patient;
   independently inflating a second chamber and a third chamber of said patient positioning assistance device to adjust the relative height of the patient's right and left sides to provide access to a predetermined body portion of the patient to a surgeon performing said surgical procedure; and
   independently inflating a fourth chamber disposed below said second and third chambers to prevent injury to nerves in the axilla of the patient in the lateral position.

16. A method to facilitate proper positioning of a patient during a surgical procedure with a patient positioning assistance device placed under the upper body of the patient in a supine position comprising:
   inflating a first chamber of said patient positioning assistance device to adjust the height of the head of said patient relative to the body of the patient;
   independently inflating a second chamber of said patient positioning assistance device to adjust the relative height of a first side of the upper body of said patient for presentation of a surgical site on Said first side to a surgeon at a desired orientation, said second chamber being substantially orthogonal to said first chamber; and
   inflating a third chamber of said patient positioning assistance device to adjust the relative height of a second side of the upper body of said patient for presentation of a surgical site on said second side to said surgeon at a desired orientation, said third chamber being substantially orthogonal to said first chamber and substantially parallel to said second chamber, said second and third chambers being on the same side of and in proximity to said first chamber.

17. The method of claim 16, further comprising substantially deflating said second chamber.

18. The method of claim 16, further comprising displacing said first chamber along at least one track disposed under said first chamber to adjust the tilt position of the head of the patient.

19. A patient positioning assistance device placed under the head and shoulders of a patient in a supine position, the device comprising:

first, second and third independently inflatable and deflatable chambers;

said first chamber being inflatable to adjust the height of the head of the patient relative to the body of the patient;

said second chamber being inflatable to adjust the height of a first side of the upper body of the patient, said second chamber being substantially orthogonal to said first chamber, and said third chamber being inflatable to adjust the height of a second side of the upper body of the patient, said third chamber being substantially orthogonal to said first chamber and substantially parallel and proximate to said second chamber, wherein said first chamber is coupled to two tracks disposed on an upper surface of a base of said patient positioning device and is operable to adjust the tilt position of the head of the patient.

20. A patient positioning assistance device placed under the head and shoulders of a patient in a lateral position, the device comprising:

a first section;

a second section substantially orthogonal to said first section;

a third section substantially orthogonal to said first section and substantially parallel to said second section;

a first platform supporting said first section and operable to adjust the height of the head of the patient relative to the body of the patient;

a second platform supporting said second section and operable to adjust the height of a first side of the upper body of the patient; and a third platform supporting said third section and operable to adjust the height of a second side of the upper body of the patient.

21. The patient positioning assistance device of claim 20, further comprising a fourth section being inflatable to adjust the height of the shoulders of said patient in the lateral position.

22. The patient positioning assistance device of claim 21, wherein said fourth section is disposed on said second and third sections.

23. The patient positioning assistance device of claim 21, wherein said fourth section is disposed below said second and third sections.

24. The patient positioning assistance device of claim 20, further comprising a fourth section being inflatable to raise the chest of said patient in the lateral position.

* * * * *